United States Patent [19]

Guberovic et al.

[11] Patent Number: 5,336,775

[45] Date of Patent: Aug. 9, 1994

[54] METHOD OF PRODUCING TERTIARY AMINE-SULPHUR-TRIOXIDE-COMPLEXES

[75] Inventors: Zeljko Guberovic, Koprivnica; Marijan Hohnjec, Zagreb; Josip Kuftinec, Hrvatski/Leskovak; Milan Oklobzija, Zagreb, all of Yugoslavia

[73] Assignee: Pfizer Inc., New York, N.Y.

[21] Appl. No.: 655,410

[22] PCT Filed: Jul. 6, 1990

[86] PCT No.: PCT/DK90/00173

§ 371 Date: Mar. 24, 1992

§ 102(e) Date: Mar. 24, 1992

[87] PCT Pub. No.: WO91/00852

PCT Pub. Date: Jan. 24, 1991

[30] Foreign Application Priority Data

Jul. 7, 1989 [CH] Switzerland ............... 2672/86-6

[51] Int. Cl.$^5$ ............... C07D 213/18; C07D 213/20; C07C 211/62
[52] U.S. Cl. ............... 546/347; 564/463
[58] Field of Search ............... 546/347; 564/463

[56] References Cited

U.S. PATENT DOCUMENTS 5,329,087 8/1993 Zeljko et al. ............... 549/317

Primary Examiner—Alan L. Rotman
Attorney, Agent, or Firm—Finnegan, Henderson, Farabow, Garrett & Dunner

[57] ABSTRACT

A process for producing tertiary amine-sulphur trioxide complexes of the general formula $$R_3N:SO_3$$

where R is a either methyl, ethyl, or propyl or the group $R_3N$ is pyridyl comprising forming a reaction mixture of chlorosulfonic acid, pyridine or other tertiary amine $R_3N$, where R is previously defined and a chlorinated organic solvent. Gaseous ammonia is passed into the reaction mixture in order to recover amine from amine hydrochloride which is formed as a by-product of the reaction. Since the amine is more soluble in the chlorinated solvent than ammonium chloride that is co-produced, the reaction of the amine with chlorosulfonic acid to produce $R_3N:SO_3$ is favored.

7 Claims, No Drawings

METHOD OF PRODUCING TERTIARY AMINE-SULPHUR-TRIOXIDE-COMPLEXES

The present invention relates to a method of producing tertiary amine-sulphur trioxide complexes of the general formula $$R_3N:SO_3,$$

where R is a methyl, ethyl, or propyl group or a moiety of a heterocyclic ring in pyridine to which chlorosulfonic acid is added to dissolve a tertiary amine in a chlorinated organic solvent.

Tertiary amine-sulphur trioxide complexes represent very important reagents which have found multiple uses, for example in the sulfation of dyes, carbohydrates and sterols or also in the sulfonation of polycyclic compounds such as acid-sensitive heterocycles (E. E. Gilbert, Chem. Rev. 549, (1961). In principle, they can be prepared by reacting sulphur trioxide with the corresponding amine in the gaseous phase or in organic solvents (U.S. Pat. No. 2,507,944, Chem. Abstr, 45, 873, 1951). However, the handling of sulphur trioxide presents great difficulties in industrial production. A method suitable for industrial use is the reaction mentioned at the outset of tertiary amine with chlorosulfonic acid in an organic solvent. But with this reaction only small yields are obtained because, of the two mols of amine used, one always combines with hydrogen chloride to form amine hydrochloride ($R_3N.HCl$). With the addition of strong alkalis, such as, e.g., sodium hydroxide, there is of course basically the possibility of again recovering the amine from the hydrochloride formed, but this is very costly and hardly economical, for the pertinent reaction is possible only in an aqueous medium. The hydrochloride ($R3N.HCl$) must first be separated from the amine-sulphur trioxide complex ($R_3N:SO_3$) by dissolving it in water and the resulting solution transferred to a separate reactor. Only then can the sodium hydroxide be added (in excess). The tertiary amine again remaining must ultimately also be separated from the water, e.g., by fractional distillation, and dried before it is again available as the starting product.

It is the object of the present invention to provide a method that is easy to handle on a commercial scale for the preparation of amine-sulphur trioxide complexes with which a considerably better yield can be achieved, in an economical manner.

According to the invention this as well as other objects are solved by a method characterized in what is stated in the characterizing portion of claim 1. Preferred embodiments of the invention are characterized in the dependent claims.

In the method pursuant to the invention, gaseous ammonia is passed into the reaction mixture in order to recover amine from amine hydrochloride previously formed as by-product. It is possible to recover the amine by means of ammonia because amine hydrochloride is more soluble than ammonium chloride. The recovered amine reacts with the chlorosulfonic acid still present to form the desired $R_3N:SO_3$ complex. In this way the amine is recovered especially advantageously in the same reaction vessel as well as in the same organic solvent.

If a tertiary amine is used which is a stronger base than ammonia, the end of the reaction is reached when the suspension is alkaline. If a tertiary amine is used which is e weaker base than ammonia, such as e.g. pyridine, ammonia is preferably passed into the reaction mixture only until the latter shows a pH of 4. With a pH above 4 the tertiary amine would be expelled by the ammonia in the desired complex, i.e., the yield would decrease.

The ammonium chloride formed can be dissolved by the addition of water and agitation. Finally, the desired tertiary amine-sulphur trioxide complex can be separated by filtration, washed and, after drying, obtained as dry final product.

As solvent, 1,2-dichloroethane, chloroform, carbon tetrachloride or methylene chloride is preferably used.

During the reaction the temperature is preferably set at a value between 0° and 30° C.

The method according to the invention exhibits the following advantages:

The reaction yield calculated on the amine used is considerably increased and readily carried out economically on a commercial scale. Yields of 80–94% can be achieved.

The specific capacity of the equipment used is doubled.

The amine is recovered in the same organic solvent and the same reaction vessel used for the desired reaction itself.

Recovery of the amine in a separate reaction vessel in aqueous solution by means of sodium hydroxide as reagent and its subsequent separation from the water is no longer required.

Energy consumption air pollution and the danger of fire are reduced.

There is lees waste and, as a result, less water pollution.

Ammonium chloride is obtained as by-product.

In the following the invention illustrated in greater detail by way of examples.

EXAMPLE 1

33.5 ml (0.507 mols) of chlorosulfonic acid is slowly added to an ice-cooled and well-stirred solution of 28.5 g (0.5 mole) of trimethylamine in 150 ml of methylene chloride. The temperature is maintained at a level below 20° C. The first half of the chlorosulfonic acid reacts highly exothermically and should therefore be added very slowly, whereas the second half requires less attention. After the entire amount of chlorosulfonic acid has been added, gaseous ammonia is passed through the solution until the pH becomes basic. With vigorous agitation, 80 ml of water is added to the suspension formed. After 15 minutes the solid product is filtered off, washed three tames with 25 ml of water each time and finally dried.

In accordance with the method described, it should be possible to prepare 55.5–66.5 g, equivalent to a yield of 80–94%, of dry final product (trimethylamine-sulphur trioxide complex).

EXAMPLE 2

The same quantity of chlorosulfonic acid as in Example 1 is added, also under the same conditions as in Example 1, to a solution of 50.5 g (0.5 mol) of triethylamine in 100 ml of methylene chloride. Again as in Example 1, ammonia is then passed through the solution, 80 ml of water is added, and the solution is filtered. The filter cake obtained is washed three times with 30 ml of methylene chloride each time. In accordance with the procedure described, it should be possible to prepare 72.95 g, equivalent to a yield of 80.61%, of dry final product (triethylamine-sulphur trioxide complex).

EXAMPLE 3

The same quantity of chlorosulfonic acid as In Example 1 is added, also under the same conditions as in Example 1, to a solution of 39.5 g (0.5 mol) pyridine in 150 ml of chloroform. As in Example 1, ammonia is then passed through the solution until the pH reaches 4.0. Further addition of ammonia would in this case diminish the yield. During the entire reaction the temperature is maintained between 15° and 20° C. To separate the ammonium chloride formed, 80 ml of water is again added and the solution stirred for 15 minutes. The solution is then filtered, the filter cake washed three times with 25 ml of water each time, and the product dried under reduced pressure.

In accordance with the procedure described, it should be possible to prepare 56.54 g, equivalent to a yield of 71.15%, of dry final product (pyridine-sulphur trioxide complex).

We claim:

1. In a process of producing tertiary amine-sulphur trioxide complexes of the general formula $$R_3N:SO_3$$

where R is a methyl, ethyl or propyl group or $R_3N$ is a pyridyl group, by adding chlorosulfonic acid to a tertiary amine in a chlorinated organic solvent to form a reaction mixture, where said tertiary amine is pyridine or $R_3N$, where R has been defined previously and in which amine hydrochloride is formed as a by-product in said reaction mixture, the improvement wherein gaseous ammonia is passed into said reaction mixture to recover said amine from amine hydrochloride in said reaction mixture.

2. A process according to claim 1 wherein said chlorinated organic solvent is 1,2-dichloroethane, carbon tetrachloride, chloroform or methylene chloride.

3. A process according to claim 2, wherein ammonia is passed into said reaction mixture at least until the pH of said reaction mixture is alkaline where said tertiary amine used is a stronger base than ammonia.

4. A process according to claim 2, wherein ammonia is passed into said reaction mixture at least until the pH of said reaction mixture reaches 4.0 where said tertiary amine used is a weaker base than ammonia.

5. Method as in one of claims 1 2, 3, or 4, wherein during the reaction the temperature is set between 0° and 30° C., preferably below 20° C. and further preferably at a level between 15° and 20° C.

6. A process according to claim 5 wherein said temperature is below 20° C.

7. A process according to claim 5 wherein said temperature is between 15° and 20° C.

* * * * *